(12) United States Patent
Gilbert et al.

(10) Patent No.: US 6,656,951 B2
(45) Date of Patent: Dec. 2, 2003

(54) 8-AZA-BICYCLO[3.2.1]OCTAN-3-OL DERIVATIVES OF 2,3-DIHYDRO-1,4-BENZODIOXAN AS 5-HT$_{1A}$ ANTAGONISTS

(75) Inventors: Adam M. Gilbert, Congers, NY (US); Gary P. Stack, Ambler, PA (US)

(73) Assignee: Wyeth, Madison, NJ (US)

( * ) Notice: Subject to any disclaimer, the term of this patent is extended or adjusted under 35 U.S.C. 154(b) by 3 days.

(21) Appl. No.: 10/128,057

(22) Filed: Apr. 23, 2002

(65) Prior Publication Data

US 2003/0032648 A1 Feb. 13, 2003

Related U.S. Application Data

(60) Provisional application No. 60/286,061, filed on Apr. 24, 2001.

(51) Int. Cl.[7] .................... A61K 31/46; A61K 31/506; C07D 451/06; A61P 25/24; A61P 25/28
(52) U.S. Cl. .................. 514/304; 546/126; 546/125; 544/335; 544/180; 544/182; 544/333; 514/256; 514/241; 514/242
(58) Field of Search .................. 546/126; 514/304, 514/256, 241, 242; 544/335, 180, 182

(56) References Cited

U.S. PATENT DOCUMENTS

| | | |
|---|---|---|
| 4,104,396 A | 8/1978 | Huebner |
| 4,129,655 A | 12/1978 | Huebner |
| 5,767,116 A | 6/1998 | Kerrigan et al. |

FOREIGN PATENT DOCUMENTS

| | | |
|---|---|---|
| JP | 11180979 | 6/1999 |
| WO | WO 90/02122 | 3/1990 |
| WO | WO 97/17343 | 5/1997 |

OTHER PUBLICATIONS

M. Carli et al., Neuropharmacology, 1999, 1165–1173, 38(8).
C. Boast et al., Neurobiology of Learning and Memory, 1999, 259–271, 71(3).
Alfredo Meneses et al., Neurobiology of Learning and Memory, 1999, 207–218, 71(2).

*Primary Examiner*—Evelyn Mei Huang
(74) *Attorney, Agent, or Firm*—Woodcock Washburn LLP

(57) ABSTRACT

Compounds of the formula:

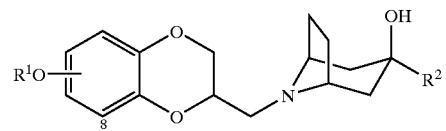

are useful for treating the cognitive deficits due to aging, stroke, head trauma, Alzheimer's disease or other neurodegenerative diseases, or schizophrenia and also treatment of disorders related to excessive serotonergic stimulation, such as anxiety, aggression and stress, and for the control of various physiological phenomena, such as appetite, thermoregulation, sleep and sexual behavior, which are known to be, at least in part, under serotonergic influence.

31 Claims, No Drawings

8-AZA-BICYCLO[3.2.1]OCTAN-3-OL DERIVATIVES OF 2,3-DIHYDRO-1,4-BENZODIOXAN AS 5-HT$_{1A}$ ANTAGONISTS

BACKGROUND OF INVENTION

This application claims priority from co-pending provisional application Ser. No. 60/286,061, filed on Apr. 24, 2001, the entire disclosure of which is hereby incorporated by reference.

Recent studies with the selective 5-HT$_{1A}$ antagonist WAY-100635 have confirmed a role for 5-HT$_{1A}$ receptors in learning and memory. Carli et. al. (Neuropharmacology (1999), 38(8), 1165–1173) demonstrated that WAY-100635 prevented the impairment of spatial learning caused by intrahippocampal injection of 3-[(R)-2-carboxypiperazin-4-yl]propyl-1-phosphonic acid (CPP), a competitive NMDA receptor antagonist, in a two-platform spatial discrimination task. Boast et al. (Neurobiol. Learn. Mem. (1999), 71(3) 259–271) found that WAY-100635 significantly reduced the cognitive impairment induced by the non-competitive NMDA antagonist MK801, as determined by the performance of rats trained on a delayed nonmatching to sample radial arm maze task. Menesis et. al. (Neurobiol. Learn. Mem. (1999), 71(2) 207–218) showed that post-training administration of WAY-100635 reversed the learning deficit induced by scopolamine, a cholinergic antagonist, in an autoshaping learning task. Novel 5-HT$_{1A}$ antagonists would be desirable for these and other uses.

DESCRIPTION OF INVENTION

In accordance with this invention, there is provided a group of novel agents which affect diseases of the central nervous system having the structural formula:

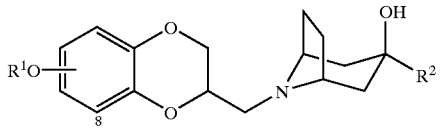

(I)

wherein

R$^1$ is a straight-chained alkyl of 1 to 6 carbon atoms, or a branched chain alkyl of 3 to 8 carbon atoms; and R$^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl, each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino in which each alkyl group has 1 to 6 carbon atoms, nitro, halo, amino, cyano, trifluoromethyl, trifluoromethoxy, and hydroxy; or a pharmaceutically acceptable salt thereof.

R$^1$ is preferably straight chain alkyl of 1 to 3 carbon atoms or a branched chain alkyl of 3 to 6 carbon atoms. Still more preferably, R$^1$ is straight chain alkyl of 1 to 2 carbon atoms.

In some embodiments of the present invention R$^2$ is phenyl, naphthyl, pyridyl, pyrimidyl, furyl, pyrrolyl, pyrazolyl, indolyl, imidazolyl, benzofuryl, or benzothienyl; each optionally substituted with 1 to 3 substituents the same or different selected from straight-chain alkyl of 1 to 3 carbon atoms, branched-chain alkyl of 3 to 6 carbon atoms, alkoxy of 1 to 3 carbon atoms, mono- or di-alkylamino in which each alkyl group has 1 to 3 carbon atoms, nitro, amino, cyano, halogen, trifluoromethyl, trifluoromethoxy, or hydroxy.

In other embodiments of the invention R$^2$ is phenyl, naphthyl, pyridyl, pyrrolyl, indolyl, or benzothienyl; each optionally substituted with 1 to 3 substituents the same or different selected from nitro, amino, cyano, halogen, trifluoromethyl, trifluoromethoxy, or hydroxy. R$^2$ is more preferably phenyl, naphthyl, benzothienyl, or pyridyl, each optionally substituted with 1 to 3 substituents the same or different selected from nitro, amino, cyano, halogen, trifluoromethyl, trifluoromethoxy, or hydroxy. In still more preferred embodiments of the invention R$^2$ is trifluoromethylphenyl or methoxyphenyl.

In some aspects of this invention the R$^1$O substituent to the 1,4-benzodioxan nucleus is at the 8-position. Examples of R$^2$ are phenyl, naphthyl, pyridyl, pyrimidyl, furyl, pyrrolyl, pyrazolyl, indolyl, imidazolyl, benzofuryl, or benzothienyl, optionally substituted with 0 to 3 substituents selected from straight-chain alkyl of 1 to 3 carbon atoms, branched-chain alkyl of 3 to 6 carbon atoms, alkoxy of 1 to 3 carbon atoms, mono- or dialkylamino in which each alkyl group has from 1 to 3 carbon atoms, nitro, amino, cyano, halogen, trifluoromethyl, trifluoromethoxy, or hydroxy.

In still other aspects of the invention the R$^1$O substituent to the 1,4-benzodioxan nucleus is at the 8-position, R$^1$ is a straight-chained alkyl of 1 to 2 carbon atoms, and R$^2$ is a phenyl, naphthyl, pyridyl, pyrrolyl, indolyl, or benzothienyl group optionally substituted with nitro, amino, cyano, halogen, trifluoromethyl, trifluoromethoxy or hydroxy.

It is understood that the definition of the compounds of formula I, when R$^1$ and R$^2$ contain asymmetric carbons, encompass all possible stereoisomers and mixtures thereof which possess the activity discussed below. This invention relates to both the R and S stereoisomers of the 2-aminomethyl-2,3-dihydro-1,4-benzodioxan, as well as to mixtures of the R and S stereoisomers. Throughout this application, the name of the product of this invention, where the absolute configuration of the 2-aminomethyl-2,3-dihydro-1,4-benzodioxan is not indicated, is intended to embrace the individual R and S enantiomers as well as mixtures of the two. In some preferred embodiments of the present invention the S stereoisomer is preferred.

Where a stereoisomer is preferred, it may in some embodiments be provided substantially free of the corresponding enantiomer. Thus, an enantiomer substantially free of the corresponding enantiomer refers to a compound which is isolated or separated via separation techniques or prepared free of the corresponding enantiomer. Substantially free as used herein means that the compound is made up of a significantly greater proportion of one stereoisomer. In preferred embodiments the compound is made up of at least about 90% by weight of a preferred stereoisomer. In other embodiments of the invention, the compound is made up of at least about 99% by weight of a preferred stereoisomer. Preferred stereoisomers may be isolated from racemic mixtures by any method known to those skilled in the art, including high performance liquid chromatography (HPLC) and the formation and crystallization of chiral salts or by methods described herein. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

Alkyl as used herein refers to an aliphatic hydrocarbon chain and includes straight and branched chains such as methyl, ethyl, n-propyl, isopropyl, n-butyl, isobutyl, secbutyl, t-butyl, n-pentyl, isopentyl, neo-pentyl, n-hexyl, and isohexyl. Lower alkyl refers to alkyl having 1 to 3 carbon atoms.

Alkoxy as used herein refers to the group R—O— where R is an alkyl group of 1 to 6 carbon atoms.

Halogen (or halo) as used herein refers to chlorine, bromine, fluorine and iodine.

Pharmaceutically acceptable salts are those derived from such organic and inorganic acids as: acetic, lactic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

Specific examples of the present invention include:
(S)-8-(8-Ethoxy-2,3-dihydro-benzo[1,4]dioxin-2-ylmethyl)-3-naphthalen-2-yl-8-aza-bicyclo[3.2.1]octan-3-ol;
(S)-8-(8-Ethoxy-2,3-dihydro-benzo[1,4]dioxin-2-ylmethyl)-3-phenyl-8-aza-bicyclo[3.2.1]octan-3-ol;
(S)-3-Benzo[b]thiophen-3-yl-8-(8-ethoxy-2,3-dihydro-benzo[1,4]dioxin-2-ylmethyl)-8-aza-bicyclo[3.2.1]octan-3-ol;
8-{[(2S)-8-Ethoxy-2,3-dihydro-benzo[1,4]dioxin-2-yl]methyl)-3-pyridin-2-yl-8-aza-bicyclo[3.2.1]octan-3-ol;
8-{[(2S)-8-Ethoxy-2,3-dihydro-benzo[1,4]dioxin-2-yl]methyl)-3-(3-trifluoromethyl-phenyl)-8-aza-bicyclo[3.2.1]octan-3-ol;
8-{[(2S)-8-Methoxy-2,3-dihydro-1,4-benzodioxin-2-yl]methyl}-3-(2-methoxyphenyl)-8-azabicyclo[3.2.1]octan-3-ol;
8-{[(2S)-8-Methoxy-2,3-dihydro-1,4-benzodioxin-2-yl]methyl}-3-[3-(trifluoromethyl)phenyl]-8-azabicyclo[3.2.1]octan-3-ol;
8-{[(2S)-8-Methoxy-2,3-dihydro-1,4-benzodioxin-2-yl]methyl}-3-(2-pyridinyl)-8-azabicyclo[3.2.1]octan-3-ol;
3-(1-Benzothien-3-yl)-8-{[(2S)-8-methoxy-2,3-dihydro-1,4-benzodioxin-2-yl]methyl}-8-azabicyclo[3.2.1]octan-3-ol;
8-{[(2S)-8-Methoxy-2,3-dihydro-1,4-benzodioxin-2-yl]methyl}-3-phenyl-8-azabicyclo[3.2.1]octan-3-ol; and
3-((2S)-8-Methoxy-2,3-dihydro-benzo[1,4]dioxin-2-ylmethyl)-8-naphthalen-2-yl-3-aza-bicyclo[3.2.1]octan-8-ol; and pharmaceutically acceptable salts thereof.

Generally, the compounds of Formula I are conveniently synthesized as described below in the following schemes and specific examples. Variables used are as defined for Formula I unless otherwise noted.

Scheme I

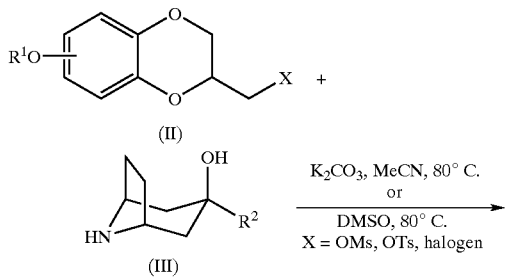

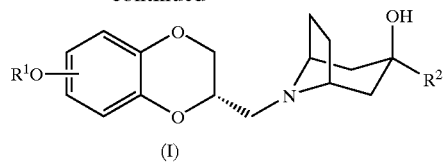

(I)

Thus 1 equiv. of benzodioxane (II) (wherein alkyl refers to branched or straight chain alkyl) is reacted with 1 equiv. of 8-aza-bicyclo[3.2.1]octan-3-ol (III) (wherein $R^2$ is aryl and aryl represents phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl) in the presence of 2 equiv. $K_2CO_3$, in MeCN at 80° C. to produce compounds of formula 1. Alternatively, 1 equiv. of benzodioxane (II) and 2 equiv. of 8-aza-bicyclo[3.2.1]octan-3-ol (III) may be combined in DMSO at 80° C. to produce compounds of Formula I.

Compounds of Formula (II) may be prepared according to Schemes II–IV.

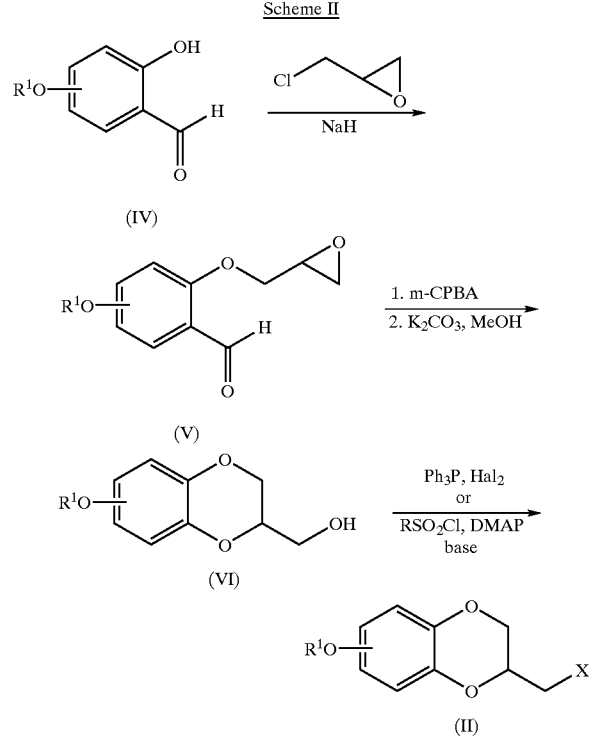

Thus salicylaldehyde (IV) can be reacted with epichlorohydrin in the presence of NaH in a suitable solvent such as THF, DMF or $Et_2O$ to produce aldehyde (V). m-CPBA oxidation of (V) to the corresponding formate, followed by hydrolysis/intramolecular epoxide opening with $K_2CO_3$ in an alcoholic solvent gives benzodioxane alcohol (VI), which can be transformed to (II) (wherein X is halogen, alkylsulfonate of 1 to 6 carbon atoms, trifluoromethanesulfonate, or benzene-sulfonate wherein the benzene ring is optionally substituted with halogen, nitro, trifluoromethyl, cyano, alkyl of 1 to 6 carbon atoms, or alkoxy of 1 to 6 carbon atoms) by reaction with $Ph_3P$/halogen ($Hal_2$) or by reaction with the appropriate sulfonyl chloride in the presence of DMAP and base.

An alternate route to (II) is presented in Scheme III.

Scheme III

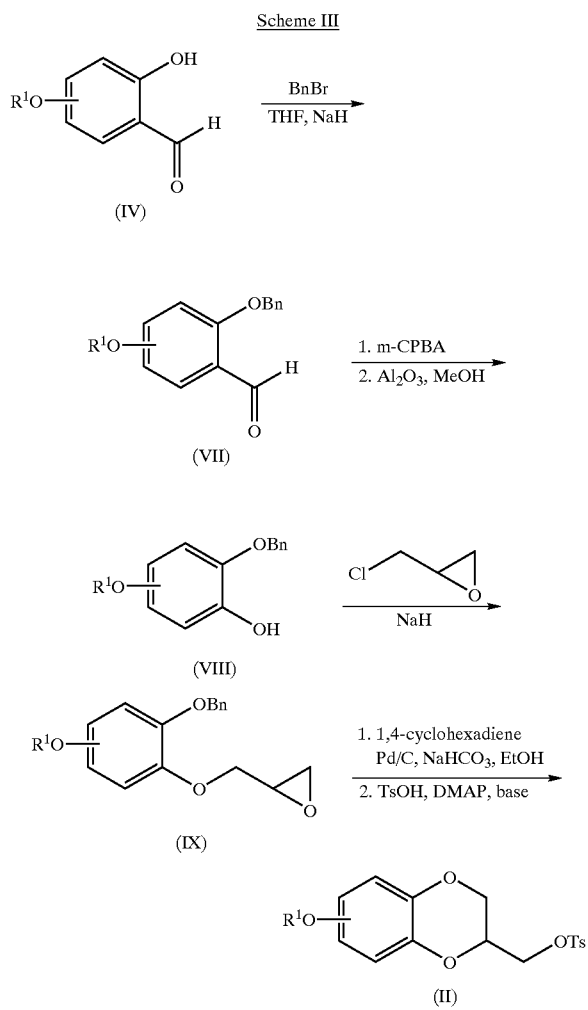

Thus salicylaldehyde (IV) may be benzylated with BnBr in the presence of base in a suitable solvent such as THF, DMF or $Et_2O$ to produce aldehyde (VII). m-CPBA oxidation to the corresponding formate, followed by hydrolysis gives phenol (VIII). Alkylation with epichlorohydrin in the presence of NaH in a suitable solvent such as THF, DMF or $Et_2O$ produces epoxide (IX). Removal of the benzyl group using transfer hydrogenation and subsequent cyclization, followed by tosylation of the resulting alcohol produces the desired tosylate (II).

An alternate route to 8-alkoxy-derivatives of (II) is presented in Scheme IV.

Scheme IV

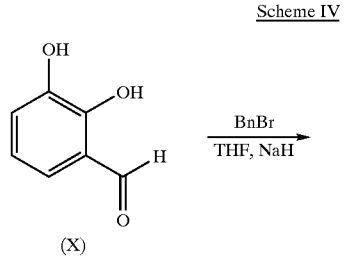

Thus 2,3-dihydroxybenzaldehyde (IX) may be selectively benzylated on the 2-hydroxyl using BnBr (where Bn is benzyl), NaH in a suitable solvent such as THF, DMF or $Et_2O$ to produce aldehyde (XI). Alkylation of the 3-hydroxyl may be accomplished using NaH, an alkyl halide ($R^1$Hal where Hal is Halogen) in a polar aprotic solvent such as DMF, NMP or DMSO. Bayer-Villager oxidation of (XII) followed by hydrolysis gives phenol (XIII). Alkylation with epichlorohydrin produces epoxide (XIV) which may be debenzylated/cyclized using transfer hydrogenation conditions. The resulting alcohol may be tosylated to give the desired compound (II).

Compounds of formula III may be prepared according to Scheme V

Scheme V

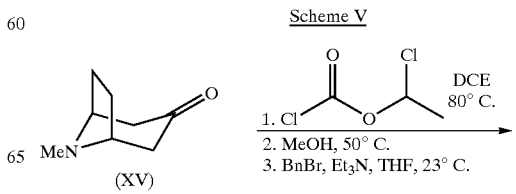

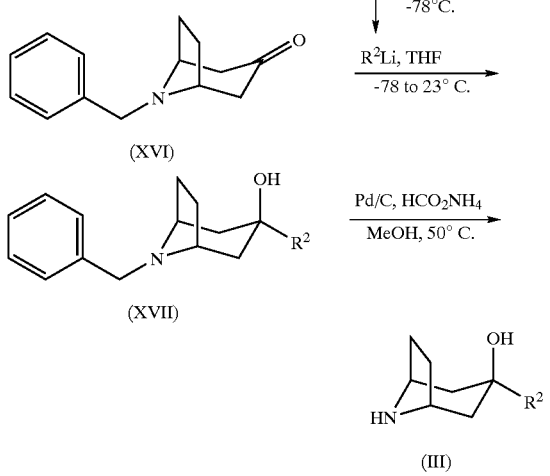

Thus tropinone (XV) may be converted to the corresponding N-benzyltropinone (XVI) by first reacting (XV) with 1-chloroethyl chloroformate in hot $CH_2Cl_2$ or $Cl(CH_2)_2Cl$ (DCE), treatment of the resulting carbamate with hot MeOH, EtOH or similar alcohols and finally treatment with BnBr, BnCl or other benzylating agents known to the skilled artisan in a solvent such as THF, benzene, DMF, or $CH_2Cl_2$ in the presence of an amine base. Benzyltropinone (XVI) may be converted to the tropinol (XVII) by reaction of (XVI) with an aryl lithium, aryl Grignard, or other aryl organometallics in a suitable solvent such as THF or $Et_2O$ at −78° C., followed by warming to room temperature. The aryl organometallics used may be obtained from aryl halides such as (XVIII). Aryl halides (XVIII) may be obtained commercially or by standard routes known to the skilled artisan. Only the product of exo addition is isolated as shown in Scheme V. The benzyl group may be removed via transfer hydrogenation of (XVII) over a precious metal catalyst such as Pd on carbon using $HCO_2NH_4$/MeOH as the source of hydrogen.

The compounds of the invention may be resolved into their enantiomers by conventional methods or, preferably, they may be prepared directly by substitution of (2R)-(−)-glycidyl 3-nitrobenzenesulfonate or tosylate (for the S benzodioxan methylamine) or (2S)-(+)-glycidyl 3-nitrobenzenesulfonate or tosylate (for the R enantiomer) in place of epichlorohydrin such as described in the schemes above.

The 5-$HT_{1A}$ affinity of compounds of this invention was established in accordance with standard pharmaceutically accepted test procedures with representative compounds as follows:

Cloning of Human 5-$HT_{1A}$ Receptor:

The PCR cloning of the human 5-$HT_{1A}$ receptor subtype from a human genomic library has been described previously (Chanda et al., 1993). A stable Chinese hamster ovary cell line expressing the human 5-$HT_{1A}$ receptor subtype (h5-$HT_{1A}$.CHO cells) was employed throughout this study. Cells were maintained in DMEM supplemented with 10% fetal calf serum, non-essential amino acids and penicillin/streptomycin.

Radioligand Binding

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at −80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 µL of buffer. Competition experiments were performed by using 7 concentrations of unlabelled drug and a final ligand concentration of 1.5 nM. Non-specific binding was determined in the presence of 10 µM 5-HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter pre-soaked for 30 minutes in 0.5% polyethyleneimine.

$^3$H-Paroxetine Binding to Assess Affinity of Drugs for the Serotonin Transporter (HC 5-$HT_{1A}$ Binding Assay):

A protocol similar to that used by Cheetham et al. (*Neuropharmacol.* 1993, 32, 737) was used to determine the affinity of compounds for the serotonin transporter. Briefly, frontal cortical membranes prepared from male S.D. rats were incubated with $^3$H-paroxetine (0.1 nM) for 60 min at 25° C. All tubes also contained either vehicle, test compound (one to eight concentrations), or a saturating concentration of fluoxetine (10 µM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallace 1205 Beta Plate® counter. Nonlinear regression analysis was used to determine $IC_{50}$ values which were converted to Ki values using the method of Cheng and Prusoff (*Biochem. Pharmacol.* 1973, 22, 3099); Ki=$IC_{50}$/((Radioligand conc.)/(1+ KD)).

Assessment of Agonism/Antagonism at the 5-$HT_{1A}$ Receptor Using [$^{35}$S]-GTPγS Binding to Cloned Human 5-$HT_{1A}$ Receptors:

The [$^{35}$S]-GTPγS binding assay was similar to that used by Lazareno and Birdsall (*Br. J. Pharmacol.* 1993, 109, 1120). Briefly, 5-$HT_{1A}$ cloned receptor membrane fragments (as used for 5-$HT_{1A}$ receptor binding assays) were stored at −70° C. until needed. When needed, membranes were rapidly thawed, centrifuged at 40,000×g for 10 minutes and resuspended at 4° C. for 10 minutes in assay buffer (25 mM HEPES, 3 mM $MgCl_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

Results from these two assays are presented below in Table I

TABLE I

3H-Paroxetine binding to assess affinity of drugs for the serotonin transporter (HC 5-HT$_{1A}$ affinity) and Assessment of agonism/antagonism at the 5-HT$_{1A}$ receptor using [$^{35}$S]-GTPγS binding to cloned human 5-HT$_{1A}$ receptors ([$^{35}$S]GTPgS)
Data for Examples 1–11.

| Example | HC 5-HT$_{1A}$ affinity n | HC 5-HT$_{1A}$ affinity K$_i$ (nm) | [$^{35}$S]GTPg S n | [$^{35}$S]GTPgS Imax, IC$_{50}$ (nM) |
|---|---|---|---|---|
| 1 | 2 | 5.9 | — | — |
| 2 | 2 | 3.1 | — | — |
| 3 | 2 | 16.7 | — | — |
| 4 | 2 | 61.6 | — | — |
| 5 | 2 | 2.9 | — | — |
| 6 | 2 | 39.0 | — | — |
| 7 | 2 | 0.33 | — | — |
| 8 | 2 | 46.0 | 1 | 100%, 1484 |
| 9 | 2 | 1.6 | 1 | 100%, 36.0 |
| 10 | 2 | 1.53 | 1 | 100%, 25.0 |
| 11 | 2 | 0.81 | 1 | 100%, 9.9 |

Thus the compounds of this invention have potent affinity for and antagonist activity at brain 5-HT$_{1A}$ serotonin receptors. The compounds of the invention are exceedingly interesting and useful for treating the cognitive deficits due to aging, stroke, head trauma, Alzheimer's disease or other neurodegenerative diseases, or schizophrenia. The compounds of the invention are also useful for the treatment of disorders related to excessive serotonergic stimulation, such as anxiety, aggression and stress, and for the control of various physiological phenomena, such as appetite, thermoregulation, sleep and sexual behavior, which are known to be, at least in part, under serotonergic influence. Finally, recent clinical trials employing drug mixtures (e.g., fluoxetine and pindolol) have demonstrated a more rapid onset of antidepressant efficacy for a treatment combining SSRI (serotonin selective reuptake inhibitor) activity and 5-HT$_{1A}$ antagonism (Artigas et. al. *Arch. Gen. Psychiat.* 1994, 51, 248 and Perez et al. *Arch. Gen. Psychiat* 1999, 56, 375). The compounds of the invention are thus interesting and useful as augmentation therapy in the treatment of depressive illness.

Thus the present invention provides methods of treating, preventing, inhibiting or alleviating each of the maladies listed above in a mammal, preferably in a human, the methods comprising providing a pharmaceutically effective amount of a compound of this invention to the mammal in need thereof.

The present invention also provides methods of augmenting the treatment of depression by providing a mammal, preferably a human with an antidepressant amount of a serotonin selective reuptake inhibitor (such as, but not limited to, sertraline, fluvoxamine, paroxetine, venlafaxine, duloxetine, citalopram, fluoxetine and metabolites thereof) and an amount of a compound of Formula I sufficient to hasten the onset of antidepressant efficacy.

Also encompassed by the present invention are pharmaceutical compositions for treating or controlling disease states or conditions of the central nervous system comprising at least one compound of Formula I, mixtures thereof, and or pharmaceutical salts thereof, and a pharmaceutically acceptable carrier therefore. Such compositions are prepared in accordance with acceptable pharmaceutical procedures, such as described in *Remingtons Pharmaceutical Sciences*, 17th edition, ed. Alfonoso R. Gennaro, Mack Publishing Company, Easton, Pa. (1985). Pharmaceutically acceptable carriers are those that are compatible with the other ingredients in the formulation and biologically acceptable.

Compounds of the present invention may further be provided in combination with an antidepressant amount of a serotonin selective reuptake inhibitor to increase the onset of antidepressant efficacy.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above e.g. cellulose derivatives, preferably sodium carboxymethyl cellulose solution), alcohols (including monohydric alcohols and polyhydric alcohols e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Oral administration may be either liquid or solid composition form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example packeted powders, vials, ampoules, prefilled syringes or sachets containing liquids. The unit dosage form can be, for example, a capsule or tablet itself, or it can be the appropriate number of any such compositions in package form.

The amount provided to a patient will vary depending upon what is being administered, the purpose of the administration, such as prophylaxis or therapy, and the state of the patient, the manner of administration, and the like. In therapeutic applications, compounds of the present invention are provided to a patient already suffering from a disease in an amount sufficient to cure or at least partially ameliorate the symptoms of the disease and its complications. An amount adequate to accomplish this is defined as a "therapeutically effective amount." The dosage to be used in the treatment of a specific case must be subjectively determined by the attending physician. The variables involved include the specific condition and the size, age and response pattern of the patient. Generally, a starting dose is about 5 mg per day with gradual increase in the daily dose to about 150 mg per day, to provide the desired dosage level in the human.

Provide as used herein means either directly administering a compound or composition of the present invention, or administering a prodrug, derivative or analog which will form an equivalent amount of the active compound or substance within the body.

The present invention includes prodrugs of compounds of Formula I. "Prodrug" as used herein means a compound which is convertible in vivo by metabolic means (e.g. by hydrolysis) to a compound of Formula I. Various forms of prodrugs are known in the art, for example, as discussed in Bundgaard, (ed.), Design of Prodrugs, Elsevier (1985); Widder, et al. (ed.), Methods in Enzymology, vol. 4, Academic Press (1985); Krogsgaard-Larsen, et al., (ed). "Design and Application of Prodrugs, Textbook of Drug Design and Development, Chapter 5, 113–191 (1991), Bundgaard, et al., Journal of Drug Deliver Reviews, 8:1–38(1992), Bundgaard, J. of Pharmaceutical Sciences, 77:285 et seq. (1988); and Higuchi and Stella (eds.) Prodrugs as Novel Drug Delivery Systems, American Chemical Society (1975).

The following examples illustrate the production of representative compounds of this invention and are not meant to limit the present invention.

EXAMPLE 1

(S)-8-(8-Ethoxy-2,3-dihydro-benzo[1,4]dioxin-2-ylmethyl)-3-naphthalen-2-yl-8-aza-bicyclo[3.2.1]octan-3-ol

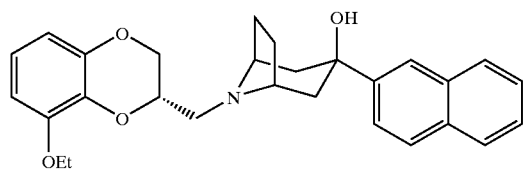

Step 1

8-Benzyl-8-aza-bicyclo[3.2.1]octan-3-one

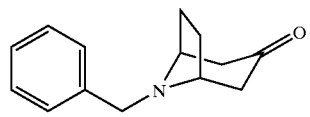

To a stirred solution of 29.2 g (209 mmol) tropinone in 300 mL 1,2-dichloroethane was added 45.5 mL (419 mmol) 1-chloroethyl chloroformate, and the resulting solution was warmed to 80° C. The reaction was monitored by TLC on a $SiO_2$ plate eluting with EtOAc/2M $NH_3$:MeOH (5:1). After stirring for 18 h, the solvent was evaporated, 300 mL MeOH was added, and the reaction was heated to reflux. After 45 min, the solvent was evaporated, then 300 mL THF, 38.83 g (227 mmol) benzyl bromide, and 33 mL (24.0 g, 237 mmol) triethylamine was added, and the resulting mixture was stirred at 23° C.

After 69 h, the mixture was transferred to a separatory funnel containing 200 mL sat. $NaHCO_3$ solution. The aqueous layer was extracted with EtOAc (2×300 mL), then the combined organics were washed with water (100 mL), brine (100 mL), dried over $MgSO_4$ filtered and evaporated to a brown oil. The crude material was purified by flash chromatography on $SiO_2$, using a gradient elution of $CH_2Cl_2$/EtOAc (40:1 to 20:1 to 8:1 to 4:1). The appropriate fractions were combined and evaporated to afford 19.91 g (92 mmol, a 44% yield) of the title compound as a yellow-orange oil. MS (ES) m/z: 216 $(MH)^+$.

Step 2

8-Benzyl-3-naphthalen-2-yl-8-aza-bicyclo[3.2.1]octan-3-ol

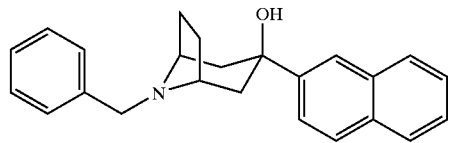

To a −78° C. solution of 10.75 g (50.35 mmol) 2-bromonaphthalene in 200 mL THF was added 20.1 mL (50.25 mmol) of n-BuLi (2.5 M in hexanes) in drops over 5 min. After 35 min, a solution of 10.51 g (48.82 mmol) 8-benzyl-8-aza-bicyclo[3.2.1]octan-3-one in 25 mL THF was added via cannula, and then allowed to warm to room temperature. After 17 h, the mixture was transferred to a separatory funnel containing 200 mL brine. The aqueous layer was extracted with EtOAc (3×150 mL), then the combined organics were washed with water (100 mL), brine (100 mL), dried over $MgSO_4$, filtered and evaporated to an orange oil.

The crude material was purified by flash chromatography on $SiO_2$, using a gradient elution of $CH_2Cl_2$/EtOAc (40:1 to 20:1 to 8:1 to 4:1 to 2:1 to 1:1). The appropriate fractions were combined and evaporated to afford 7.07 g (20.6 mmol, a 42% yield) of the title compound as a yellow oil. MS (ES) m/z: 345 $(MH)_+$.

Step 3

3-Naphthalen-2-yl-8-aza-bicyclo[3.2.1]octan-3-ol

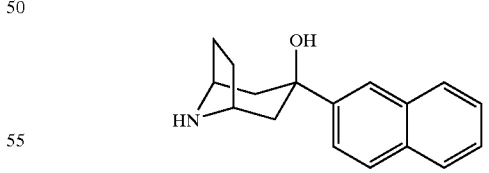

To 3.80 g (11.1 mmol) 8-benzyl-3-naphthalen-2-yl-8-aza-bicyclo[3.2.1]octan-3-ol was added 1.20 g (19.0 mmol) of ammonium formate, 100 mL MeOH, and 2.46 g Pd/C (10 wt. %). The reaction mixture was heated to 50° C., and was monitored by TLC on a $SiO_2$ plate with $CHCl_3$:MeOH (10:1). After 21 h, the mixture was cooled to room temperature, filtered through a pad of celite and evaporated to afford 2.0 g (7.9 mmol, a 72% yield) of the title compound as an off-white solid. MS (ES) m/z: 344 $(MH)^+$.

Step 4

(S)-8-(8-Ethoxy-2,3-dihydro-benzo[1,4]dioxin-2-ylmethyl)-3-naphthalen-2-yl-8-aza-bicyclo[3.2.1]octan-3-ol

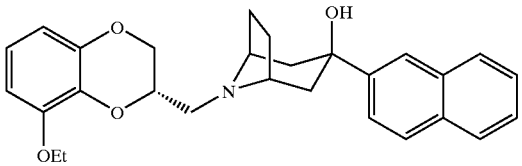

To 117 mg (0.32 mmol) (S)-toluene-4-sulfonic acid 8-ethoxy-2,3-dihydro-benzo[1,4]dioxin-2-ylmethyl ester was added 84 mg (0.33 mmol) 3-naphthalen-2-yl-8-azabicyclo[3.2.1]octan-3-ol, 95.0 mg $K_2CO_3$, and 7 mL acetonitrile. The reaction was refluxed and was monitored by TLC on a silica gel plate using $CHCl_3$:MeOH (10:1) as eluent. After 18 h, the mixture was transferred to a separatory funnel containing 50 mL water. The aqueous layer was extracted with $CH_2Cl_2$ (2×25 mL), washed with brine, dried over $Na_2SO_4$, filtered and evaporated to an oil. The crude material was purified by flash chromatography on silica gel, using a gradient elution of $CHCl_3$:MeOH (40:1 to 20:1). The appropriate fractions were combined and evaporated to afford 68.1 mg (0.15 mmol, a 48% yield) of the title compound as a tan solid.

The oxalate salt of the title compound was prepared by adding 8.1 mg (0.09 mmol) of oxalic acid to 38.7 mg (0.09 mmol) of the title compound in 0.75 mL EtOH at 23° C. After stirring for 16 h, $Et_2O$ was added which precipitated an off-white solid. The solid was collected and washed with $Et_2O$ to afford 32.0 mg (0.06 mmol, a 67% yield) of the oxalate salt. mp: 126–129° C.; MS (ES) m/z: 446 (MH)+.

EXAMPLE 2

(S)-8-(8-Ethoxy-2,3-dihydro-benzo[1,4]dioxin-2-ylmethyl)-3-phenyl-8-aza-bicyclo[3.2.1]octan-3-ol

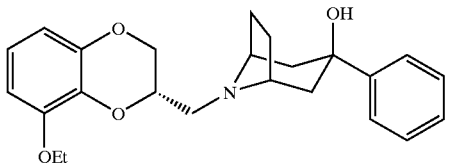

Step 1

8-Benzyl-3-phenyl-8-azabicyclo[3.2.1]octan-3-ol

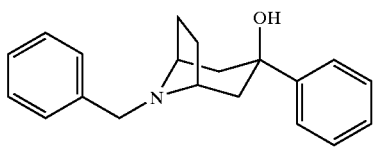

The title compound was prepared according to the procedure of Example 1, Step 2 using bromobenzene in place of 2-bromonaphthalene. Yield: 64%, colorless oil; MS (ES) m/z: 294 (MH)+.

Step 2

3-Phenyl-8-azabicyclo[3.2.1]octan-3-ol

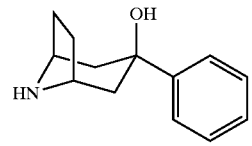

The title compound was prepared according to the procedure of Example 1, Step 3. Yield: 75%, white solid; MS (ES) m/z: 204 (MH)+.

Step 3

(S)-8-(8-Ethoxy-2,3-dihydro-benzo[1,4]dioxin-2-ylmethyl)-3-phenyl-8-aza-bicyclo[3.2.1]octan-3-ol

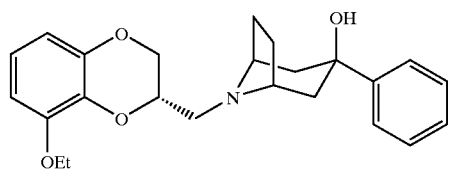

The title compound was prepared by the same procedure described in Example 1, Step 4 using 3-phenyl-8-azabicyclo[3.2.1]octan-3-ol (92.0 mg 0.45 mmol) in place of 3-naphthalen-2-yl-8-aza-bicyclo[3.2.1]octan-3-ol. Yield: 52% (86.0 mg, 0.22 mmol); tan solid.

The oxalate salt was prepared in the manner previously described in Example 1, Step 4 using 42.2 mg (0.11 mmol) of the title compound. Yield: 82% (42.8 mg, 0.088 mmol); off-white solid. mp: 152–155° C.; MS (ES) m/z: 396 (MH)+. Anal. Cald. for $C_{24}H_{29}NO_4$: C, 64.28; H, 6.43; N, 2.88. Found C, 62.41; H, 6.34; N, 2.79.

EXAMPLE 3

(S)-3-Benzo[b]thiophen-3-yl-8-(8-ethoxy-2,3-dihydro-benzo[1,4]dioxin-2-ylmethyl)-8-aza-bicyclo[3.2.1]octan-3-ol

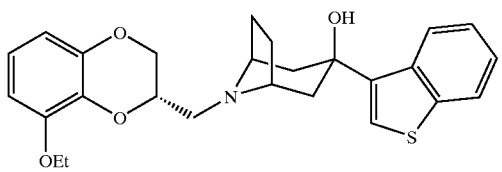

Step 1

8-Benzyl-3-phenyl-8-azabicyclo[3.2.1]octan-3-ol

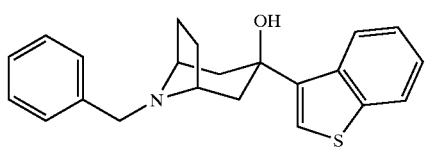

The title compound was prepared according to the procedure of Example 1, Step 2 using 3-bromobenzothiophene in place of 2-bromonaphthalene. Yield: 81%; MS (ES) m/z: 350 (MH)+.

Step 2

3-Benzo[b]thiophen-3-yl-8-aza-bicyclo[3.2.1]octan-3-ol

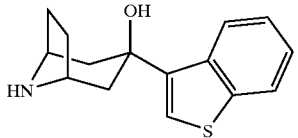

The title compound was prepared according to the procedure of Example 1, Step 3. Yield: 49%, white solid; MS (ES) m/z: 260 (MH)$^+$.

Step 3

(S)-3-Benzo[b]thiophen-3-yl-8-(8-ethoxy-2,3-dihydro-benzo[1,4]dioxin-2-ylmethyl)-8-aza-bicyclo[3.2.1]octan-3-ol

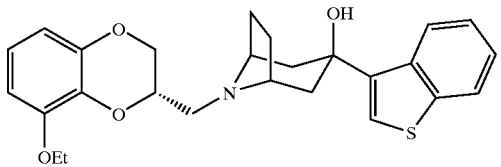

The title compound was prepared by the same procedure described in Example 1, Step 4 using 3-benzo[b]thiophen-3-yl-8-aza-bicyclo[3.2.1]octan-3-ol (117.9 mg 0.45 mmol) in place of 3-naphthalen-2-yl-8-aza-bicyclo[3.2.1]octan-3-ol. Yield: 15% (30.0 mg, 0.066 mmol); tan solid.

The oxalate salt was prepared in the manner previously described in Example 1, Step 4 using 30.0 mg (0.066 mmol) of the title compound and CH$_2$Cl$_2$/EtOH (2:1) in place of EtOH. Yield: 36% (13.0 mg, 0.024 mmol); off-white solid. mp: 111–114° C.; MS (ES) m/z: 452 (MH)$^+$.

EXAMPLE 4

8-{[(2S)-8-Ethoxy-2,3-dihydro-benzo[1,4]dioxin-2-yl]methyl)-3-pyridin-2-yl-8-aza-bicyclo[3.2.1]octan-3-ol

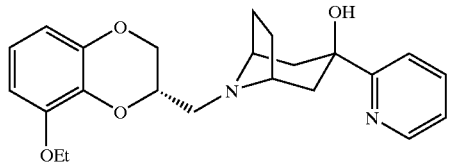

Step 1

8-Benzyl-3-(2-pyridinyl)-8-azabicyclo[3.2.1]octan-3-ol

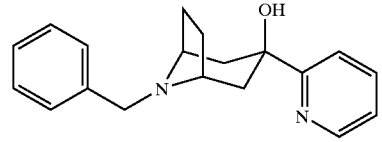

The title compound was prepared according to the procedure of Example 1, Step 2 using 2-bromopyridine in place of 2-bromonaphthalene. Yield: 56%, colorless oil; MS (ES) m/z 295 (MH)$^+$.

Step 2

3-(2-Pyridinyl)-8-azabicyclo[3.2.1]octan-3-ol

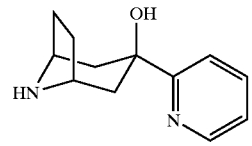

The title compound was prepared according to the procedure of Example 1, Step 3. Yield: 67%, white solid; MS (ES) m/z: 205 (MH)$^+$.

Step 3

8-(8-Ethoxy-2,3-dihydro-benzo[1,4]dioxin-2-ylmethyl)-3-pyridin-2-yl-8-aza-bicyclo[3.2.1]octan-3-ol

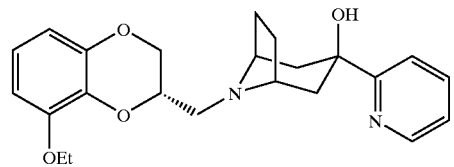

The title compound was prepared by the same procedure described in Example 1, Step 4 using 3-(2-pyridinyl)-8-azabicyclo[3.2.1]octan-3-ol (101.0 mg 0.49 mmol) in place of 3-naphthalen-2-yl-8-aza-bicyclo[3.2.1]octan-3-ol. Yield: 37% (70.8 mg, 0.18 mmol); yellow crystalline solid.

The oxalate salt was prepared in the manner previously described in Example 1, Step 4 using 42.0 mg (0.11 mmol) of the title compound and CH$_2$Cl$_2$/EtOH (2:1) in place of EtOH. Yield: 59% (30.6 mg, 0.06 mmol); off-white solid. mp: 95–99° C.; MS (ES) m/z: 398 (MH)$^+$.

EXAMPLE 5

8-{[(2S)-8-Ethoxy-2,3-dihydro-benzo[1,4]dioxin-2-yl]methyl)-3-(3-trifluoromethylphenyl)-8-azabicyclo[3.2.1]octan-3-ol

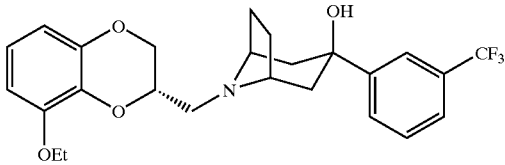

Step 1

8-Benzyl-3-(3-trifluoromethylphenyl)-8-azabicyclo[3.2.1]octan-3-ol

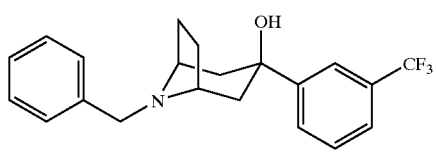

The title compound was prepared according to the procedure of Example 1, Step 2 using 2-bromopyridine in place of 2-bromonaphthalene. Yield: 66%, colorless oil; MS (ES) m/z: 362 (MH)$^+$.

Step 2

3-(3-Trifluoromethylphenyl)-8-azabicyclo[3.2.1]octan-3-ol

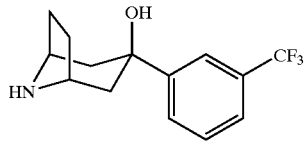

The title compound was prepared according to the procedure of Example 1, Step 3. Yield: 67%, white solid; MS (ES) m/z: 272 (MH)$^+$.

Step 3

8-{([(2S)-8-Ethoxy-2,3-dihydro-benzo[1,4]dioxin-2-yl]methyl)-3-(3-trifluoromethylphenyl)-8-azabicyclo[3.2.1]octan-3-ol

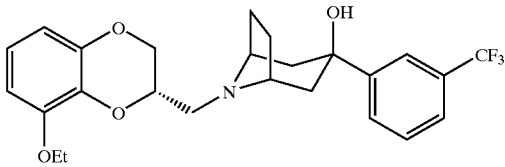

The title compound was prepared by the same procedure described in Example 1, Step 4 using 3-(3-trifluoromethylphenyl)-8-aza-bicyclo[3.2.1]octan-3-ol (71.5 mg 0.26 mmol) in place of 3-naphthalen-2-yl-8-aza-bicyclo[3.2.1]octan-3-ol. Yield: 78% (91 mg, 0.20 mmol); yellow oil.

The oxalate salt was prepared in the manner previously described in Example 1, Step 4 using 90.4 mg (0.20 mmol) of the title compound and CH$_2$Cl$_2$/EtOH (2:1) in place of EtOH. Yield: 51% (54.7 mg, 0.099 mmol); off-white solid. mp: 86–90° C.; MS (ES) m/z: 464 (MH)$^+$.

EXAMPLE 6

8-{[(2S)-8-Methoxy-2,3-dihydro-1,4-benzodioxin-2-yl]methyl}-3-(2-methoxyphenyl)-8-azabicyclo[3.2.1]octan-3-ol

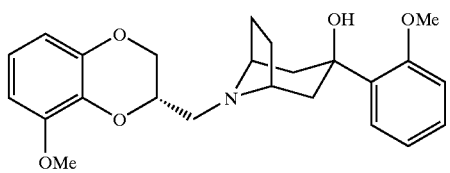

Step 1

8-Benzyl-3-(3-trifluoromethylphenyl)-8-azabicyclo[3.2.1]octan-3-ol

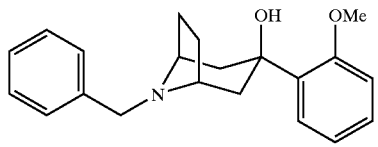

The title compound was prepared according to the procedure of Example 1, Step 2 using 2-bromoanisole in place of 2-bromonaphthalene. Yield: 50%, colorless oil; MS (ES) m/z: 362 (MH)$^+$.

Step 2

3-(2-Methoxyphenyl)-8-azabicyclo[3.2.1]octan-3-ol

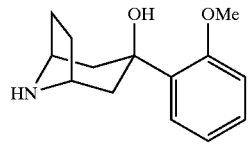

The title compound was prepared according to the procedure of Example 1, Step 3. Yield: 44%, white solid; MS (ES) m/z 272 (MH)$^+$.

Step 3

8-{[(2S)-8-Methoxy-2,3-dihydro-1,4-benzodioxin-2-yl]methyl}-3-(2-methoxyphenyl)-8-azabicyclo[3.2.1]octan-3-ol

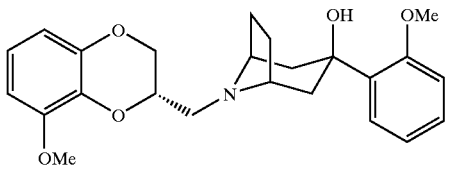

The title compound was prepared by the same procedure described in Example 1, Step 4 using 3-(2-methoxyphenyl)-8-azabicyclo[3.2.1]octan-3-ol in place of 3-naphthalen-2-yl-8-aza-bicyclo[3.2.1]octan-3-ol, and (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 70%, white solid.

The oxalate salt was prepared in the manner previously described in Example 1, Step 4. Yield: 75%, off-white solid. mp: 176–178° C.; MS (ES) m/z: 412 (MH)+.

EXAMPLE 7

8-{[(2S)-8-Methoxy-2,3-dihydro-1,4-benzodioxin-2-yl]methyl}-3-[3-(trifluoromethyl)phenyl]-8-azabicyclo[3.2.1]octan-3-ol

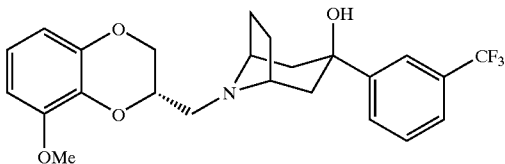

The title compound was prepared by the same procedure described in Example 1, Step 4 using 3-(3-trifluromethylphenyl)-8-azabicyclo[3.2.1]octan-3-ol in place of 3-naphthalen-2-yl-8-aza-bicyclo[3.2.1]octan-3-ol, and (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 68%, white solid.

The oxalate salt was prepared in the manner previously described in Example 1, Step 4. Yield: 81%, off-white solid. mp: 104–107° C.; MS (ES) m/z: 450 (MH)+.

EXAMPLE 8

8-{[(2S)-8-Methoxy-2,3-dihydro-1,4-benzodioxin-2-yl]methyl}-3-(2-pyridinyl)-8-azabicyclo[3.2.1]octan-3-ol

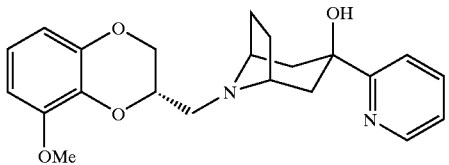

The title compound was prepared by the same procedure described in Example 1, Step 4 using 3-(2-pyridinyl)-8-azabicyclo[3.2.1]octan-3-ol in place of 3-naphthalen-2-yl-8-aza-bicyclo[3.2.1]octan-3-ol, and (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 70%, white solid.

The oxalate salt was prepared in the manner previously described in Example 1, Step 4. Yield: 59%, off-white solid. mp: 107–110° C. (dec.); MS (ES) m/z: 383 (MH)+.

EXAMPLE 9

3-(1-Benzothien-3-yl)-8-{[(2S)-8-methoxy-2,3-dihydro-1,4-benzodioxin-2-yl]methyl}-8-azabicyclo[3.2.1]octan-3-ol

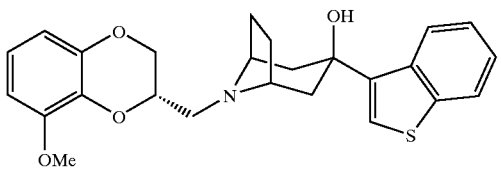

The title compound was prepared by the same procedure described in Example 1, Step 4 using 3-benzo[b]thiophen-3-yl-8-aza-bicyclo[3.2.1]octan-3-ol in place of 3-naphthalen-2-yl-8-aza-bicyclo[3.2.1]octan-3-ol, and (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 33%, white solid.

The oxalate salt was prepared in the manner previously described in Example 1, Step 4. Yield: 64%, off-white solid. mp: 162–164° C.; MS (ES) m/z: 439 (MH)+.

EXAMPLE 10

8-{[(2S)-8-Methoxy-2,3-dihydro-1,4-benzodioxin-2-yl]methyl}-3-phenyl-8-azabicyclo[3.2.1]octan-3-ol

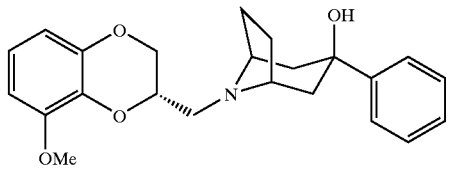

The title compound was prepared by the same procedure described in Example 1, Step 4 using 3-phenyl-8-azabicyclo[3.2.1]octan-3-ol in place of 3-naphthalen-2-yl-8-aza-bicyclo[3.2.1]octan-3-ol, and (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 76%, white solid.

The oxalate salt was prepared in the manner previously described in Example 1, Step 4. Yield: 92%, off-white solid. mp: 113–115° C.; MS (ES) m/z: 382 (MH)+.

EXAMPLE 11

3-((2S)-8-Methoxy-2,3-dihydro-benzo[1,4]dioxin-2-ylmethyl)-8-naphthalen-2-yl-3-aza-bicyclo[3.2.1]octan-8-ol

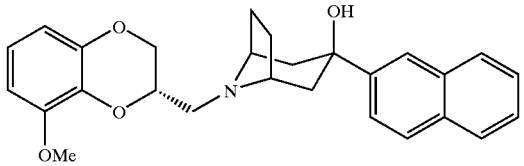

The title compound was prepared by the same procedure described in Example 1, Step 4 using (S)-toluene-4-sulfonic acid 8-methoxy-2,3-dihydro-benzo[1,4]dioxin-2-ylmethyl ester in place of (S)-toluene-4-sulfonic acid 8-ethoxy-2,3-dihydro-benzo[1,4]dioxin-2-ylmethyl ester. Yield: 56%, white solid.

The oxalate salt was prepared in the manner previously described in Example 1, Step 4. Yield: 67%, off-white solid. mp: 129–132° C.; MS (ES) m/z: 433 (MH)$^+$.

What is claimed is:

1. A compound of Formula I:

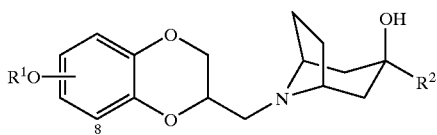

wherein
  $R^1$ is a straight-chained alkyl of 1 to 6 carbon atoms, or a branched chain alkyl of 3 to 8 carbon atoms; and
  $R^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl, each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino in which each alkyl group has 1 to 6 carbon atoms, nitro, halo, amino, cyano, trifluoromethyl, trifluoromethoxy, and hydroxy;
  and pharmaceutically acceptable salts thereof.

2. A compound of claim 1 wherein $R^1$ is a straight-chained alkyl of 1 to 3 carbon atoms, or a branched chain alkyl of 3 to 6 carbon atoms.

3. A compound of claim 1 wherein $R^1$ is a straight-chained alkyl of 1 or 2 carbon atoms.

4. A compound of claim 1 wherein $R^2$ is phenyl, naphthyl, pyridyl, pyrimidyl, furyl, pyrrolyl, pyrazolyl, indolyl, imidazolyl, benzofuryl, or benzothienyl; each optionally substituted with 1 to 3 substituents the same or different selected from straight-chain alkyl of 1 to 3 carbon atoms, branched-chain alkyl of 3 to 6 carbon atoms, alkoxy of 1 to 3 carbon atoms, mono- or di-alkylamino in which each alkyl group has 1 to 3 carbon atoms, nitro, amino, cyano, halogen, trifluoromethyl, trifluoromethoxy, and hydroxy.

5. A compound of claim 1 wherein $R^2$ is phenyl, naphthyl, pyridyl, pyrrolyl, indolyl, or benzothienyl; each optionally substituted with 1 to 3 substituents the same or different selected from nitro, amino, cyano, halogen, trifluoromethyl, trifluoromethoxy, and hydroxy.

6. A compound of claim 1 wherein $R^2$ is trifluoromethylphenyl or methoxyphenyl.

7. A compound of claim 1 wherein the $R^1O$ substituent is bonded to the 1,4-benzodioxan nucleus is at the 8 position.

8. A compound of claim 1 wherein $R^1$ is a straight-chained alkyl of 1 to 3 carbon atoms, or a branched chain alkyl of 3 to 6 carbon atoms and $R^2$ is phenyl, naphthyl, pyridyl, pyrimidyl, furyl, pyrrolyl, pyrazolyl, indolyl, imidazolyl, benzofuryl, or benzothienyl; each optionally substituted with 0 to 3 substituents selected from straight-chain alkyl of 1 to 3 carbon atoms, branched-chain alkyl of 3 to 6 carbon atoms, alkoxy of 1 to 3 carbon atoms, mono- or di-alkylamino in which each alkyl group has 1 to 3 carbon atoms, halogen, trifluoromethyl, trifluoromethoxy, and hydroxy.

9. A compound of claim 1 wherein $R^1$ is a straight-chained alkyl of 1 or 2 carbon atoms, and $R^2$ is phenyl, naphthyl, pyridyl, pyrrolyl, indolyl, or benzothienyl; each optionally substituted with a 0 to 3 substituents selected from nitro, amino, cyano, halogen, trifluoromethyl, trifluoromethoxy, and hydroxy.

10. A compound of claim 1 wherein $R^1$ is a straight chain alkyl of 1 or 2 carbon atoms and $R^2$ is trifluoromethylphenyl or methoxyphenyl.

11. A compound of claim 1 which is (S)-8-(8-ethoxy-2,3-dihydrobenzo-[1,4]dioxin-2-ylmethyl)-3-naphthalen-2-yl-8-aza-bicyclo[3.2.1]octan-3-ol or a pharmaceutically acceptable salt thereof.

12. A compound of claim 1 which is (S)-8-(8-ethoxy-2,3-dihydro-benzo[1,4]dioxin-2-ylmethyl)-3-phenyl-8-aza-bicyclo[3.2.1]octan-3-ol or a pharmaceutically acceptable salt thereof.

13. A compound of claim 1 which is (S)-3-benzo[b]thiophen-3-yl-8-(8-ethoxy-2,3-dihydro-benzo[1,4]dioxin-2-ylmethyl)-8-aza-bicyclo[3.2.1]octan-3-ol or a pharmaceutically acceptable salt thereof.

14. A compound of claim 1 which is 8-{[(2S)-8-ethoxy-2,3-dihydrobenzo-[1,4]dioxin-2-yl]methyl)-3-pyridin-2-yl-8-aza-bicyclo[3.2.1]octan-3-ol or a pharmaceutically acceptable salt thereof.

15. A compound of claim 1 which is 8-{[(2S)-8-ethoxy-2,3-dihydrobenzo-[1,4]dioxin-2-yl]methyl)-3-(3-trifluoromethyl-phenyl)-8-aza-bicyclo[3.2.1]octan-3-ol or a pharmaceutically acceptable salt thereof.

16. A compound of claim 1 which is 8-{[(2S)-8-methoxy-2,3-dihydro-1,4-benzodioxin-2-yl]methyl}-3-(2-methoxyphenyl)-8-azabicyclo[3.2.1]octan-3-ol or a pharmaceutically acceptable salt thereof.

17. A compound of claim 1 which is 8-{[(2S)-8-methoxy-2,3-dihydro-1,4-benzodioxin-2-yl]methyl}-3-[3-(trifluoromethyl)phenyl]-8-azabicyclo[3.2.1]octan-3-ol or a pharmaceutically acceptable salt thereof.

18. A compound of claim 1 which is 8-{[(2S)-8-methoxy-2,3-dihydro-1,4-benzodioxin-2-yl]methyl}-3-(2-pyridinyl)-8-azabicyclo[3.2.1]octan-3-ol or a pharmaceutically acceptable salt thereof.

19. A compound of claim 1 which is 3-(1-benzothien-3-yl)-8-{[(2S)-8-methoxy-2,3-dihydro-1,4-benzodioxin-2-yl]methyl}-8-azabicyclo[3.2.1]octan-3-ol or a pharmaceutically acceptable salt thereof.

20. A compound of claim 1 which is 8-{[(2S)-8-methoxy-2,3-dihydro-1,4-benzodioxin-2-yl]methyl}-3-phenyl-8-azabicyclo[3.2.1]octan-3-ol or a pharma-ceutically acceptable salt thereof.

21. A compound of claim 1 which is 3-((2S)-8-methoxy-2,3-dihydrobenzo-[1,4]dioxin-2-ylmethyl)-8-naphthalen-2-yl-3-aza-bicyclo[3.2.1]octan-8-ol or a pharmaceutically acceptable salt thereof.

22. A method of treating a subject suffering from a condition selected from the group consisting of cognitive deficits, or schizophrenia which comprises providing to the subject suffering from said condition, a therapeutically effective amount of a compound of formula I

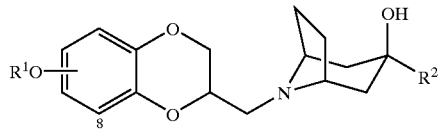

(I)

wherein
$R^1$ is a straight-chained alkyl of 1 to 6 carbon atoms, or a branched chain alkyl of 3 to 8 carbon atoms; and
$R^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl, each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino in which each alkyl group has 1 to 6 carbon atoms, nitro, halo, amino, cyano, trifluoromethyl, trifluoromethoxy, and hydroxy;
and pharmaceutically acceptable salts thereof.

23. The method of claim 22 wherein the subject is a human.

24. A method of treating a subject suffering from a condition selected from the group consisting of anxiety, aggression and stress which comprises providing to the subject suffering from said condition, a therapeutically effective amount of a compound of formula I

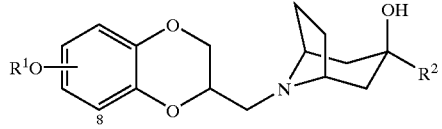

(I)

wherein
$R^1$ is a straight-chained alkyl of 1 to 6 carbon atoms, or a branched chain alkyl of 3 to 8 carbon atoms; and
$R^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl, each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino in which each alkyl group has 1 to 6 carbon atoms, nitro, halo, amino, cyano, trifluoromethyl, trifluoromethoxy, and hydroxy;
and pharmaceutically acceptable salts thereof.

25. The method of claim 24 wherein the subject is a human.

26. A method of treating a subject suffering from depression comprising providing to the subject suffering from said condition, an antidepressant amount of a serotonin selective reuptake inhibitor and an amount of a compound of formula I

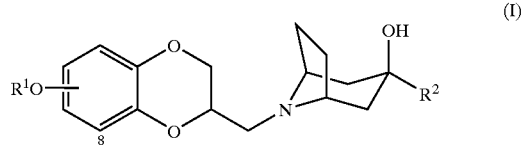

(I)

wherein
$R^1$ is a straight-chained alkyl of 1 to 6 carbon atoms, or a branched chain alkyl of 3 to 8 carbon atoms; and
$R^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino of 1 to 6 carbon atoms, nitro, halo, amino, cyano, trifluoromethyl, trifluoromethoxy, and hydroxy;
and pharmaceutically acceptable salts thereof, said amount of compound of Formula I being effective to increase the onset of antidepressant efficacy.

27. The method of claim 26 wherein the subject is a human.

28. The method of claim 26 wherein the serotonin selective reuptake inhibitor is sertraline, fluvoxamine, paroxetine, venlafaxine, duloxetine, citalopram, fluoxetine or metabolites thereof.

29. A pharmaceutical composition comprising a compound of Formula I

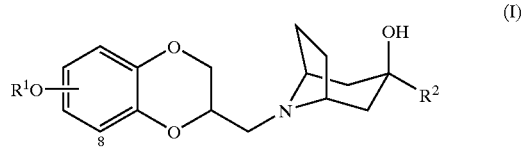

(I)

wherein
$R^1$ is a straight-chained alkyl of 1 to 6 carbon atoms, or a branched chain alkyl of 3 to 8 carbon atoms; and
$R^2$ is phenyl, naphthyl, anthracyl, phenanthryl, pyridyl, pyrimidyl, triazinyl, furyl, pyrrolyl, pyrazolyl, indolyl, imidazolyl, benzofuryl, benzothienyl, oxazolyl, or thiazolyl each optionally substituted with 0 to 3 substituents selected from straight-chain alkyl of 1 to 6 carbon atoms, branched-chain alkyl of 3 to 8 carbon atoms, alkoxy of 1 to 6 carbon atoms, mono- or dialkylamino of 1 to 6 carbon atoms, nitro, halo, amino, cyano, trifluoromethyl, trifluoromethoxy, and hydroxy;
and pharmaceutically acceptable salts thereof; and a pharmaceutically acceptable carrier or excipient.

30. The composition of claim 29 further comprising an antidepressant amount of a serotonin selective reuptake inhibitor.

31. The composition of claim 30 wherein the serotonin selective reuptake inhibitor is sertraline, fluvoxamine, paroxetine, venlafaxine, duloxetine, citalopram, fluoxetine or metabolites thereof.

* * * * *